United States Patent
Hennig et al.

(10) Patent No.: US 11,046,950 B2
(45) Date of Patent: *Jun. 29, 2021

(54) MAGNETIC PARTICLES WITH A CLOSED ULTRATHIN SILICA LAYER, METHOD FOR THE PRODUCTION THEREOF AND THEIR USE

(71) Applicant: Siemens Healthcare Diagnostics GmbH, Eschborn (DE)

(72) Inventors: Guido Hennig, Cologne (DE); Karlheinz Hildenbrand, Krefeld (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 68 days.

This patent is subject to a terminal disclaimer.

(21) Appl. No.: 16/386,828

(22) Filed: Apr. 17, 2019

(65) Prior Publication Data

US 2019/0241885 A1     Aug. 8, 2019

Related U.S. Application Data

(60) Continuation of application No. 15/434,355, filed on Feb. 16, 2017, now Pat. No. 10,385,331, which is a
(Continued)

(30) Foreign Application Priority Data

Jun. 23, 2005  (EP) ..................................... 05013522

(51) Int. Cl.
    *C12N 15/10*     (2006.01)
    *H01F 1/36*      (2006.01)
    (Continued)

(52) U.S. Cl.
    CPC ....... *C12N 15/1013* (2013.01); *C12Q 1/6806* (2013.01); *H01F 1/01* (2013.01);
    (Continued)

(58) Field of Classification Search
    CPC ............ C12Q 2563/143; C12Q 1/6813; C12Q 1/703; C12Q 1/6806; C12N 15/10;
    (Continued)

(56) References Cited

U.S. PATENT DOCUMENTS 6,235,270 B1   5/2001   Ishii et al.
6,548,264 B1   4/2003   Weihong et al.
(Continued)

FOREIGN PATENT DOCUMENTS

CN   101031513   9/2007
CN   101172256   5/2008
(Continued)

OTHER PUBLICATIONS

Donselaar et al "Concentration-dependent sedimentation of dilute magnetic fluids and magnetic silic dispersions" Langmuir, 1997, 13:6018-6025. (Year: 1997).*

(Continued)

Primary Examiner — Betty J Forman (57) ABSTRACT

A method for producing silicate-containing magnetic particles having a closed and tight silicate layer and high purity. In addition, the novel method prevents an uncontrolled formation of aggregates and clusters of silicates on the magnetite surface, thereby having a positive influence on the properties and biological applications. The method enables depletion of nanoparticulate solid substance particles on the basis of a fractionated centrifugation. The silicate-coated magnetic particles exhibit optimized magnetization and suspension behavior as well as advantageous run-off behavior from plastic surfaces. These highly pure magnetic particles coated with silicon dioxide are preferably used for isolating nucleic acids from cell and tissue samples, whereby the separating out from a sample matrix ensues by means of magnetic fields. The particles are particularly well suited for (Continued)

the automatic purification of nucleic acids, mostly from biological body samples for the purpose of analyzing them with different amplification methods.

10 Claims, 2 Drawing Sheets

Related U.S. Application Data division of application No. 14/626,311, filed on Feb. 19, 2015, now Pat. No. 9,617,534, which is a continuation of application No. 11/917,922, filed as application No. PCT/EP2006/005677 on Jun. 13, 2006, now abandoned.

(51) Int. Cl.

| | | |
|---|---|---|
| *C12Q 1/6806* | (2018.01) | |
| *H01F 41/00* | (2006.01) | |
| *H01F 1/01* | (2006.01) | |
| *H01F 1/11* | (2006.01) | |

(52) U.S. Cl.
CPC ............. *H01F 1/36* (2013.01); *H01F 41/005* (2013.01); *H01F 1/112* (2013.01)

(58) Field of Classification Search
CPC .. C12N 15/1013; G01N 33/5434; H01F 1/36; H01F 1/01; C04B 35/62807; C04B 35/62897
See application file for complete search history.

(56) References Cited

U.S. PATENT DOCUMENTS

| | | | | |
|---|---|---|---|---|
| 7,524,630 | B2 | 4/2009 | Tan et al. | |
| 8,323,899 | B2* | 12/2012 | Sherman | B82Y 25/00 |
| | | | | 435/6.12 |
| 8,703,931 | B2* | 4/2014 | Euting | C07B 63/00 |
| | | | | 536/25.4 |
| 8,846,897 | B2* | 9/2014 | Euting | B03C 1/288 |
| | | | | 536/25.4 |
| 10,385,331 | B2* | 8/2019 | Hennig | C12N 15/1013 |
| 2002/0182598 | A1* | 12/2002 | Zhang | C12Q 1/6834 |
| | | | | 435/6.1 |
| 2004/0067503 | A1* | 4/2004 | Tan | C12Q 1/6816 |
| | | | | 435/6.1 |
| 2004/0126902 | A1 | 7/2004 | Nishiya et al. | |
| 2004/0215011 | A1 | 10/2004 | Deggerdal et al. | |
| 2006/0062999 | A1 | 3/2006 | Arai | |

FOREIGN PATENT DOCUMENTS

| | | |
|---|---|---|
| EP | 0988853 | 3/2000 |
| JP | 2004-500067 | 1/2003 |
| JP | 20003104996 | 4/2003 |
| JP | 2003-533363 | 11/2003 |
| JP | 2005017013 | 1/2005 |
| JP | 2005-069955 | 3/2005 |
| JP | 20005286315 | 10/2005 |
| JP | 2006523027 | 10/2006 |
| WO | 0188540 | 11/2001 |
| WO | 03058649 | 7/2003 |

OTHER PUBLICATIONS

Phillipse et al., Magnetic silica dispersions: preparation and stability of surface-modified silica particles with magnetic core, Langmuir, 10:92-99 (1994).
Liu et al: "A Novel Two-Step Silica-Coating Process for Engineering Magnetic Nanocomposites", Chem. mater. 10: 3936-3940, (1998).
Bohmann et al., RNA Extraction from Archival Fomalin-Fixed Paraffin-Embedded Tissue: A comparison of Manual, Semi-automated, and Fully Automated Purification methods, Clin. Chem. 55(9): 1719-1727 (2009) and WO A 03/058649.
Bruce Ian J. et al. "Synthesis, characterisation and application of silica-magnetite nanocomposites," Journal of Magnetism and Magnetic Materials, 284:145-160, (2004).
Dynal, "Biomagnetic Techniques in Molecular Biology," Technical Handbook, 3rd edition, (1998), pp. 34-36.

\* cited by examiner

MAGNETIC PARTICLES WITH A CLOSED ULTRATHIN SILICA LAYER, METHOD FOR THE PRODUCTION THEREOF AND THEIR USE

RELATED APPLICATIONS

This application is a continuation application of, and claims priority from, U.S. application Ser. No. 15/434,355 filed Feb. 16, 2017 which is a divisional application of, and claims priority from, U.S. application Ser. No. 14/626,311 filed Feb. 19, 2015 which is a continuation application of, and claims priority from, U.S. application Ser. No. 11/917,922 filed Nov. 17, 2009 which is a 371 application of, and claims priority from, PCT Application PCT/EP2006/005677, filed Jun. 13, 2006 which claims priority from European Patent Application Serial No. 05013522.7, filed Jun. 23, 2005, all of which are titled "MAGNETIC PARTICLES WITH A CLOSED ULTRATHIN SILICA LAYER, METHOD FOR THE PRODUCTION THEREOF AND THEIR USE," and each of which is hereby incorporated by reference herein in their entirety.

In recent times, molecular diagnostics have become increasingly important. Molecular diagnostics have entered into the clinical diagnosis of illnesses. This includes the measurement of molecular markers to improve the diagnosis of a disease, early detection, the monitoring of an illness during therapy, the prognosis of illnesses and the prediction of effects or side-effects of medicines (including the detection of infective agents, detection of mutations of the genome, the prediction of effects and side-effects of medicines on the basis of predetermined genetic patterns or those acquired in the course of an illness, detection of circulating tumor cells and the identification of risk factors for predisposition to an illness). Methods of molecular diagnosis have meanwhile also been used in veterinary medicine, analysis of the environment and foodstuff testing. A further application area is investigations by pathological/cytological institutes or in the course of forensic investigations. Genetic diagnosis has meanwhile also been used as part of healthcare (e.g. investigation of banked blood for freedom from infective agents), and legislation is planned to regulate such tests. Methods which are also used in clinical molecular diagnosis (such as hybridization or amplification techniques such as PCR (polymerase chain reaction), TMA (transcription mediated amplification), LCR (ligase chain reaction), bDNA (branched DNA) or NASBA (nucleic acid sequence based amplification) also form part of routine procedures in basic scientific work.

A precondition for performing an assay in molecular diagnostics is generally the isolation of DNA or RNA from the sample to be analyzed. There are of course analysis methods, such as bDNA-based tests that enable nucleic acid isolation and detection reaction to be carried out at the same time but PCR, as the most widely used molecular biological method in molecular diagnostics, almost always requires the use of previously purified nucleic acids because of their capacity to be influenced by exogenic factors.

The conventional preparation process for nucleic acids is in this case based on a fluid-fluid extraction. An example of this is the phenol-chloroform extraction of DNA from body samples. However, the great effort required and the need to sometimes perhaps use highly toxic substances means that this method has fallen considerably into disfavor in recent years compared with solid-phase based methods.

With the use of solid-phase based extraction methods for nucleic acids, the sample preparation can be subdivided into the actual analysis operation, largely independent of the particular problem, into four basic steps: 1. Conditioning of the solid phase; 2. Selective or specific bonding of the analytes to the solid phase and removal of the remaining sample matrix; 3. Washing out any impurities from the solid phase and 4. Elution of the enriched and purified analytes.

The well known property of nucleic acids to bond specifically to silicate-containing adsorbents such as glass powder [Proc. Natl. Acad. USA 76 (1979) 615-619, Anal. Biochem. 121 (1982) 382-387], diatomaceous earth [Methods Enzymol. 65 (1979) 176-182] or native silicon dioxide [J. Clin. Microbiol. 28 (1990) 495-503, EP 0 389 063 B1] under chaotropic or high-salt conditions, i.e. at high concentrations of chaotropes or other salts, has long been used for the selective and reversible bonding of nucleic acids. With the aid of a buffer containing water-soluble organic solvent, usually a low aliphatic alcohol, impurities are then washed from the adsorbent, the carrier is dried and the adsorbed nucleic acids are eluated with distilled water or a so-called low-salt buffer, i.e. a buffer with a low ion strength.

In view of the complete and cost-effective automation of nucleic acid isolation, methods with super-paramagnetic adsorbents play an increasingly important role.

In the simplest example (WO 01/46404), commercially produced magnetic particles produced for technical applications, such as electrographic toners, are used directly for nucleic acid preparation without further modification.

Products of this kind produced by technical mass production do, however, meet one of the most important preconditions, such as a specific nucleic acid absorption and magnetisability. On the other hand, these commercially available products are unable to meet important boundary conditions that are indispensable for highly-sensitive and reproducible results. For example, it is of decisive importance in the field of virus diagnostics (e.g. HCV or HIV) to extract the viral nucleic acids quantitatively from the serum or plasma, i.e. with almost 100% yield, in order from this to derive an accurate virus concentration in the serum/plasma and thus make decisions with regard to therapy. The purity of the magnetic particles also plays a decisive role with regard to optical evaluation. Especially with magnetite particles that are frequently still micro-porous, diffusion of iron atoms from the particles can lead to colored solutions that can severely disturb the transmission or reflection measurements.

For this reason, various developments of magnetic particles for biological applications, particularly with regard to the manual and automated isolation of nucleic acid, are described.

In this case, magnetic particles that support a high density of SiOH groups on the surface play an outstanding role. It is known that SiOH groups can form reversible bonds with nucleic acids. Silica-modified magnetic particles are also the object of this invention.

To obtain highly-sensitive, quantitative and reproducible results, such magnetic particles must, in addition to magnetizability and the capacity to bond with nucleic acid, fulfill further boundary conditions, which are described in more detail in the following.

Particle Size and Particle Size Distribution:

It has been shown that magnetic particles of $Fe_3O_4$ (magnetite), for electrographic toner with primary particle sizes of approximately 0.1 to 1 µm, e.g. available from the Lanxess company under the name Bayoxide E, meet almost ideal preconditions with regard to particle size. Such particle sizes enable the important boundary condition of "suspension stability" important for biological applications to be achieved. This must on the one hand be sufficiently resistant to ensure that no significant sedimentation occurs within a few minutes, for example ten to fifteen minutes (adsorption of nucleic acids) after shaking, whereas the magnetic particles loaded with nucleic acids must be able to be completely separated as regards the shortest possible analysis times within a few minutes, for example within one to five minutes.

However, the available magnetic particles of $Fe_3O_4$ (magnetite) unfortunately still have ongoing deficiencies in this respect, in that small amounts of very fine magnetite particles in the nanometer range are still present.

These unwanted by-products that because of their large surface can bond considerable amounts of nucleic acids are unfortunately not separated in the magnetic field within a few minutes and thus the information content of these nucleic acids, especially with regard to the quantitative measurement of nucleic acids, can be lost.

In addition to these losses in yield, this also often leads to unclear, often yellow-brown, supernatants that can not only negatively influence the commercial marketing but can also interfere with the photometric evaluation of the eluates.

It would therefore be of great advantage if this "nanoparticle magnetite particulate component" could be separated for the biological application described here.

Silicate Content:

As mentioned above, some magnetic particles produced on a large technical scale, for example the Bayoxide E series from the Lanxess company, still have a certain nucleic acid bonding capacity even without special silica post-treatment, because they are produced in bulk and therefore also support SiOH groups on the surface in small amounts. Because of the low nucleic acid adsorption capacity, such products require corresponding relatively large amounts of magnetic particles, which means that the preparation of small sample volumes is hampered.

Furthermore, such products have a wetting behavior of vessel walls, such as glass or plastic walls of microtiter plates such as are routinely used for nucleic acid purification, that is unfavorable for the application described here. Therefore substantial amounts of the unmodified, relatively hydrophobic magnetic particles remain adsorbed in aqueous suspensions on the microtiter plate walls and thus lead to inaccuracies in pipetting and loss of yield.

Particles with a high density of SiOH surface groups, which because of their hydrophilicity very advantageously roll off plastic walls in particular, such as the aforementioned microtiter plates, behave very favorably in this respect.

With many magnetic particle developments for the isolation of nucleic acid, the silica proportion is accordingly dominant compared with the magnetite proportion. As, for example, described in WO 01/71732, silica particles that can be magnetized by the magnetite inclusion are obtained by hydrolysis from reactive silica compounds such as tetraethoxysilane (TEOS) in the presence of magnetite particles. Because of the high density of SiOH groups on the surface, such particles however show a high nucleic acid bonding capacity and a favorable wetting behavior of the microtiter plate walls, but on the other hand the magnetic properties are very heavily reduced corresponding to the reduced magnetite content. Furthermore, the magnetic silica particles produced in this way have significantly more unfavorable morphological properties, such as very heterogeneous particle sizes and particle size distribution and it should be mentioned that large non-spherical particles can lead to blockages during automatic pipetting.

Extractable Components:

The nucleic acids isolated using the magnetic particle process are generally subject to further processes such as a PCR (polymerase chain reaction), TMA (transcription mediated amplification), LCR (ligase chain reaction) or NASBA (nucleic acid sequence based amplification). These are highly-sensitive, enzyme-controlled processes that can be disturbed by numerous impurities and iron compounds, that, for example, can act as enzyme toxins.

Therefore, the magnetic particles produced for the nucleic acid purification must fulfill particular purity requirements. If iron oxides, such as Bayoxide from the Lanxess company produced using technical mass production, are used this problem is certainly not insignificant because the magnetite particles have a certain porosity and surface roughness. Therefore, impurities can become included in the micropores both from the process of iron oxide production and in the succeeding silica treatment that as enzyme toxins or in the case of colored impurities can interfere with the photometric evaluation during subsequent processes.

OBJECT OF THIS INVENTION

The object of this invention is to produce, on the basis of commercially available magnetic particles, silica-modified magnetic particles with a high density of SiOH surface groups and a closed and tight surface layer of silicate. Neither the morphology nor the very good magnetic properties of the initial products should be substantially influenced by the silica modification. Equally, the wetting behavior on plastic surfaces should be positively influenced by the silica coating. Furthermore, the silica-modified magnetic particles should be optimized with regard to extractable impurities to the extent that the release of impurities or iron compounds from the magnetite core is prevented and no interference is possible with either the biological detection reactions or the photometric evaluation.

On the basis of Bayoxide E magnetic particles from the Lanxess company, WO 03/058649 describes a smart process for silica deposition on the particle surface using sodium silicate solutions, for example sodium silicate HK 30 from the Cognis company. By a gradual dilution of the pH value in the Bayoxide E/sodium silicate, equivalent to a gradual pH shift from strong alkaline (pH11.5) to neutral (pH7), a careful deposition of silica on the magnetic particle surface takes place. If, as mentioned in WO 03/058649, the pH reduction takes place due to the addition of acids (WO 98/31840), uncontrolled conversion of sodium silicate into silica ($SiO_2$) can occur at the acid infusion point with magnetic particles becoming stored in the structure of the silica, so that the aforementioned controlled silica deposition on the magnetic particle surface is by no means achieved. Nonetheless, the formation of minute silica aggregates or clusters on the surface cannot be completely prevented by the "batch method" described in WO 03/058649.

Whereas the silica-modified magnetic particles described in WO 03/058649 have good properties with regard to surface structure and nucleic acid bonding behavior, very disadvantageous yellow-brown supernatants can be observed in the long-term behavior (after standing for a few weeks) of the relevant aqueous suspensions. In biological assays during which surfactants are generally used, this effect can be observed even after short stand times. An analysis shows that, in addition to sodium silicate components, traces of iron compounds and very fine magnetite particles can be found in these colored supernatants. Clearly, these impurities became locked into the porous magnetic particle structure through the silica surface, from where they diffuse outwards in the course of time. These observations also indicate that the silicate layer is not completely closed or is irregularly distributed by the batch method described in WO 03/058649 and therefore cannot prevent the release of iron compounds.

DESCRIPTION

In view of the elimination of the aforementioned extractable impurities, the technical process described in the following was optimized, with the progress compared with the method described in WO 03/058649 being documented. However, with the tests described here, in contrast to the examples of WO 03/058649, Bayoxide E 8707, which is no longer available as a standard product, was replaced by the very similar Bayoxide E 8706 type. In both cases it is $Fe_3O_4$ magnetite that has a low Si content due to its production, with type 8707 having an Fe/Si content of 99.1/0.9 and Bayoxide E 8706 having 99.4/0.4. The surface quality, particularly the pH value of the $Fe_3O_4$ magnetite, is important for the method according to the invention. Whereas Bayoxide E 8707 with a pH of 6.5 has a slightly acid surface, a neutral pH value, or depending on the batch even a slightly alkali value (pH 7.5), is found with the Bayoxide E 8706 now used. Surprisingly, it was found that even these slightly alkali surface properties can induce sodium silicate deposition. Normally, the silica deposition takes place from the very alkali sodium silicate solutions by the addition of acids.

Comparison tests then surprisingly showed that distinctly better results could be obtained with regard to extractable components if instead of the gradual pH reduction described in WO 03/058649 a continuous method, such as a membrane method was used. In this case, as described in more detail in the examples, the aqueous sodium silicate/magnetic particle suspension was purified after a reaction time of one hour using "cross flow microfiltration". Cross flow microfiltration, which is carried out at a slight negative pressure, is, as described in "Basic Principles of Membrane Technology" by M. Mulder, a known separation or purification method. In this case the work is carried out at constant volumes, i.e. the permeate volume flow containing the impurities is replaced by the same volume flow of incoming fresh water. In contrast to the dialysis method known in biology, depending on the pore diameter not only low-molecular salts but also particulate impurities are separated during microfiltration. This continuous cleaning process was continued until the quality of the outflowing permeate quality corresponded to the degree of purity of the incoming fresh water, which took approximately 12 to 15 hours depending on the size of the preparation.

During the analytical surface characterization using ESCA it was very surprising to find that the silica-modified magnetic particles produced in this way have a novel, i.e. ultrathin, silica structure on the silica surface, with which the improved purification or increased purity can be correlated. This silica nanolayer is characterized by a silica layer of up to 5 nm distributed uniformly over the complete particle surface. Furthermore, the method according to the invention however also describes a layer thickness of 2 nm and also, quite particularly preferred, layer thicknesses of 0.5 nm to 0.2 nm. The particles coated in this way have a surface coating which is characterized in that it, for example, prevents the escape of irons into the surrounding solution.

The production of magnetic particles with a silica layer thickness of 0.2 nm is described in example 3.

Furthermore, the inventive method is characterized by a closed and tight silica layer, which is also associated with the improved purity or reduced observed contamination effect in the supernatant. The purity of these silica-coated magnetic particles produced according to the inventive method is substantially better compared with the method described in WO 03/058649. Thus, visible discoloration of the supernatant after production and washing no longer occurs (see examples 2 and 3). In particular, the tight and closed silica layer prevents the escape of visible, or also invisible, impurities, for example iron ions, which can disturb the amplification methods or the optical evaluation of biological experiments (see examples 4 and 5).

Furthermore, it was surprising to find that the formation of aggregates and clusters of silicates on the magnetite surface was almost completely prevented due to the slow and continuous dilution and thus reduction of the pH value to neutral values in the described membrane filtration process and/or again strongly reduced compared to the "batch method" described in WO 03/058649. This well defined nanolayer of silicon positively influences the properties and biological applications described in the following.

Furthermore, it was also found that additional product optimization with respect to clear supernatants could be achieved by carrying out a fractionated centrifugation, which enabled a separation of slowly sedimenting iron oxide particles, after the membrane process.

With the samples produced in this way, which are treated as aqueous suspensions, all criteria such as a magnetisability absolutely identical to the initial product, unchanged morphology, high nucleic acid bonding capacity, favorable roll-off from the walls of the microtiter plates and outstanding stability of the suspension with trouble-free separation of the magnetic particles in the magnetic field within a few minutes without significant impurities in the supernatant are achieved.

The expression "magnetic particles coated with silica" includes magnetite cores that are coated with a nanolayer of silica.

The expression "closed and tight silica layer" includes a uniform, homogenous single to multiple molecular silica layer in a range of less than 5 nm, with a layer thickness of 2 nm being particularly preferred and a layer thickness of 0.5 to 0.2 nm being quite particularly preferred. This closed silica layer particularly prevents the release of iron compounds and iron ions to the environment of the silica-coated magnetic particle.

The expression "improved methods of production" includes a washing process with the aid of a micro- or ultra-filtration unit that is easy to perform but is very intensive and leads to extreme purity of the silica-coated magnetic particle. With this method, a slow, controlled and continuous dilution, and therefore a reduction of the pH value to neutral pH values in the reaction solution, occurs after an initial precipitation of the nanolayer of silicate onto the particle surface, thus forming an extremely uniform, tight, closed and homogenous layer of silicate on the surface of the magnetite. Furthermore, unwanted formations of aggregates or clusters of silicates are prevented or largely reduced.

The expression "depletion of nano particulate components with the aid of the centrifugation technique" includes the application of centrifugation techniques or simple gravitational techniques. This produces sedimentation of the required fractions, with it being possible to reject the unwanted nano particulate components by removing the supernatant. By determining the particle size distribution using ultra-centrifugation, this effect can be detected by means of the depleted minute fractions. With the centrifugation technique, the initial suspension is centrifuged for fifteen minutes at approximately 3000 g, the supernatant is removed and an equal amount of water or buffer is added and then re-suspended and this step is repeated several times (up to ten times). The gravitation technique simply means that instead of the centrifugation a long time is allowed to elapse until a large proportion of the particles have settled on the bottom of the vessel and the aqueous supernatant is then replaced.

The expression "optimum magnetization behavior" includes the property of the inventive particles to have the largest possible amount of magnetite and thus be completely separated from the sample matrix during the purification within a few minutes, for example within one to five minutes, when a magnetic field is applied from outside to a reaction vessel. This is particularly noteworthy with respect to the shortest possible purification times in an automated process using a pipetting robot and for the use of the cheapest possible magnets with a limited magnetic field strength as hardware components.

The expression "suspension behavior" includes the property of the inventive particles to behave in such a way that due to an optimum grain size distribution no significant sedimentation occurs within a few minutes, for example ten to fifteen minutes (adsorption phase of the nucleic acids) after shaking during the purification phase.

The expression "optimum run-off behavior from plastic surfaces" includes the property the inventive particles have of a low affinity to the plastic articles used in biological purification processes due to a hydrophilic surface quality. The plastic articles used mainly include polystyrene, polyethylene and polypropylene vessels or "microtiter" plates of comparable plastics of any shape or size. The specific silica layer of the inventive magnetic particles enables a repelling interaction with these plastic surfaces, so that the coated magnetic particles roll off these surfaces and undergo no great interactions, which in the end could lead to a loss of yield during a biological purification process of nucleic acids.

The expression "isolation" means the purification of nucleic acids from a biological sample using the aforementioned silica-coated magnetic particles and is divided into the following steps.

a) Dissolving the sample in a reaction vessel with a lysis buffer and, after incubation, adding a bonding buffer, which preferably contains chaotropic salts, with guanidin(ium)isothiocyanate being particularly preferred, of high molarity
b) Adding silicate-coated magnetic particles
c) Incubating at a temperature at which the nucleic acid bonds to the magnetic particles
d) Removing constituents that are not bonded from the reaction preparation by applying a magnetic field, which separates the magnetic particles from the surrounding fluid
e) Applying a washing buffer several times followed by the removal of said buffer with magnetization of the particles for cleaning unspecifically bonded molecules from the nucleic acid
f) Adding an elution buffer under conditions in which the nucleic acid is separated from the magnetic particles
g) Separating the eluate with the nucleic acid after re-application of a magnetic field.

The expression "automated purification" includes variations of these processes in which the manual labour by humans is replaced either completely or only partially in steps, especially with the biological body sample being dissolved with a special buffer during the steps, the addition of magnetic particles, the incubation at a specific temperature, the removal of non-absorbed sample constituents, the washing steps, the elution of bonded nucleic acids from the particles at a specific temperature and the separation of the eluate from the particle suspension.

The expression "nucleic acids" includes oligomer and polymer ribonucleotides or 2'-desoxy-ribonucleotides with a chain length of more than 10 monomer units. The monomer units in nucleic acids are linked by phosphoric acid diester compounds between 3'- and 5'-hydroxyl groups of adjacent monomer units and the 1'-atom of the respective carbohydrate component is glycosidically bonded to a heterocyclic base. Nucleic acids can form double and triple strands due to the development of intermolecular hydrogen bridge bonds.

This also includes protein/nucleic acid complexes and nucleic acids with synthetic nucleotides such as morpholinos or PNAs (peptide-nucleic acids).

The expression "biological body sample" includes biological material containing nucleic acid, such as whole blood, blood serum or blood plasma, especially serum or plasma containing a virus, very particularly serum samples infected with HIV and HCV, "Buffy Coat" (white blood cell fraction of the blood), faeces, ascites, swabs, sputum, organ aspirates, biopsies, tissue sections, in this case very particularly differently fixed tissue sections, especially those fixed with fixing agents containing formalin, and paraffin-embedded tissue sections, secretions, liquor, bile, lymphatic fluid, urine, stool, sperm, cells and cell cultures. This can also include nucleic acids that originate from biochemical processes and are then to be purified.

The expression "detection with various amplification methods" includes the duplication of purified nucleic acids using various molecular-biological technologies, especially PCR, transcription-mediated amplification (TMA), LCA or also NASBA and the succeeding or simultaneous detection of the amplification products. This also includes detection using signal amplification methods such as of bDNA, i.e. without nucleic acid amplification. Detection of the PCR in particular can be carried out by the application of kinetic methods with the aid of fluorescence technology under real-time conditions or can be carried out using a conventional agarose gel. The real-time PCR in particular enables a very good quantitative determination of nucleic acids by using suitable calibrators. What is critical and limiting for clinical sensitivity (avoidance of false negative results) in this case is the efficient purification of the nucleic acids (i.e. efficient bonding to the magnetic particle and the reversible release under PCR-compatible conditions).

A further object of the invention is a kit for performing a method according to the invention that contains the following components:

(a) Reagents for dissolving the sample
(b) Magnetic particles containing silica or a suspension of magnetic particles containing silica
(c) Washing buffer
(d) Elution buffer The above lists and the following examples are applicable for the individual components. Single or several components of the kit can also be used in a modified form.

With this invention it is possible by using specially produced silica-coated magnetic particles to detect nucleic acids particularly efficiently, automatically and quantitatively from biological body sample purifications using appropriate amplification techniques. In some embodiments, the silica-coated magnetic particles have a grain size distribution between 0.1 μm and 1 μm.

This invention thus represents an important contribution to nucleic acid diagnostics.

EXAMPLES

The following are examples of protocols for performing the described invention. Exact reaction conditions for the respective nucleic acids to be purified are given in these examples, but nevertheless various parameters such as magnetic particle quantity, incubation temperature and washing temperature, incubation and washing times and the concentration of lysis buffer, washing buffer and elution buffer can vary depending on the particular nucleic acid to be purified.

Example 1

Production of silicate-coated magnetite particles from Bayoxide E 8706 using sodium silicate 37/40 by the gradual reduction of the pH value (similar to the method in WO 03/058649 A1)
Reaction Part:
   4000 g of sodium silicate solution 37/40 (Cognis GmbH) is placed in a 6 l three-neck flask with a KPG stirrer. 2000 g of Bayoxide 8706 (Bayer AG) is added within ten minutes whilst stirring. Stirring then continues for one hour at room temperature.
Purification:
   After the stirrer is switched off, the silica-coated magnetite beads settle. This process can be accelerated if necessary by applying a magnetic field. After a waiting time of one hour, the supernatant is drawn off. For purification, 4 l of water is added whilst stirring for approximately ten minutes. The supernatant is again drawn off. This washing process is repeated at least four times until the last wash water has achieved a pH value of 7.5-7.0.
Properties of the Silica-Magnetic Particles:
   Zeta potential: −50.2
   Silica content according to ESCA 7.0 atom % Si
   Purity: The supernatant was colored yellow/brown after standing ten days at room temperature.

Example 2

Production of super-pure silica-coated magnetite particles from Bayoxide E 8706 using sodium silicate 37/40 with a continuous reduction of the pH value by cross flow microfiltration.

The reaction part described in Example 1 was repeated but the processing took place not gradually or batchwise but instead with the aid of the "Centramate®" micro filtration unit from PALL with a 0.2 μm Supor® membrane cassette.

For this purpose, the magnetic particle suspension was drawn off via a hose by means of a pump and passed through the membrane cassette, with the permeate being rejected but the retentate being fed back into the reaction vessel. The amount equivalent to the permeate was then resupplied to the particle suspension.

After a filtration time of 12 h, the pH and conductivity of the permeate had achieved the quality of the original water and the cleaning process was ended.
Properties of the End Product:
   Zeta potential: −41 mV
   Si content: 4.9 atom % Si determined according to ESCA 1.
   Silica content of the starting product Bayoxide 8706: 2.4 atom % Si
   The differential amount, 2.5 atom % Si, was accordingly deposited on the surface of the particles by silica treatment using sodium silicate. This produces a silica layer thickness of 0.4 nm.
Purity:
   The particle suspension purified by ultrafiltration showed no discoloration in the supernatant even after standing for several months at room temperature.

Example 3

Production of super-pure silicate-coated magnetite particles from Bayoxide E 8706 and sodium silicate 37/40 with a continuous reduction of the pH value by cross flow microfiltration followed by fractionated centrifugation The end product described in Example 2 was centrifuged for seven minutes at 3225 g with the aid of a centrifuge (Eppendorf 5810). Whereas the main part (>98%) of the product was sedimented, a dark brown colored supernatant remained that was discarded.

The residue was again added to water, centrifuged and separated from the colored supernatant. This fractionated centrifugation was repeated eight times until the supernatant became colorless.
Properties of the End Product (Ninth Centrifugate):
   Zeta potential: −35 mV
   Si content: 3.0% Si.
   The differential amount, 0.6 atom %, was accordingly deposited on the particle surface by silica treatment with sodium silicate. This resulted in a silicon layer thickness of 0.2 nm.
Purity:
   The supernatant of the magnetic particle suspension produced in this way remained completely colorless even after storing for several months.
   This product quality showed outstanding values particularly with regard to magnetic separation. Thus, after applying a magnet an absolutely clear supernatant was observed after less than twenty seconds.

Example 4

Figure 1:
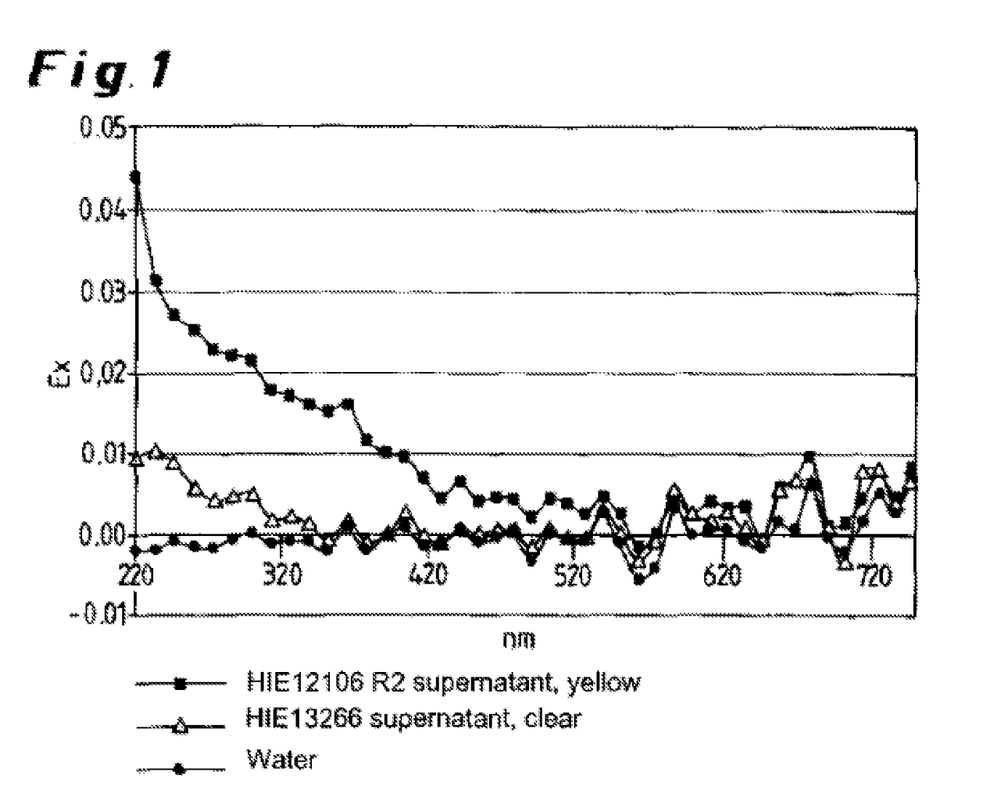
FIG. 1 illustrates absorption spectra of aqueous supernatants of the silica-coated magnetic particles versus water.

Optical measurement of aqueous supernatants from silica-coated magnetic particle suspensions In this experiment, the absorption spectra of two aqueous supernatants of the silica-coated magnetic particles with lot designation HIE13266 (originating from the inventive method of Example 2) and 3) and lot designation HIE12106R2 (originating from the method from WO 03/058649 A1, based on Bayoxide E 8707) were recorded in a range of 221-750 nm using a spectrometer from the Nanodrop company (see FIG. 1).

A water spectrum drawn from these spectra was used as a reference. A water spectrum was again taken as a sample for control purposes (zero line).

From the spectra, it could be seen that the aqueous supernatants of the silica-coated magnetic particles HIE13266 had an absorption behavior similar to water. On the other hand, the absorption lines of the supernatants of HIE12106R2 showed a clearly changed and elevated absorption behavior up to a range of approximately 500 nm.

From this it can be seen that the new inventive production method with continuous washing (particles HIE13266) in a microfiltration unit led to reduced contamination effects or the occurrence of iron compounds in the supernatant compared to particles HIE12106R2 with sequential multiple washing or gradual reduction of the pH value (see also WO 03/058649 A1). These contamination effects with particles HIE12106R2 manifest themselves by visible discoloration of the supernatants over time and also increased absorption behavior. Furthermore, these reduced contamination effects in the supernatant from the method according to the invention indicate a closed silica layer on the particles.

Example 5

Behavior of aqueous supernatants of silica-coated magnetic particles using RT-PCR.

The aqueous supernatants of the two differently silica-coated magnetic particles (lot designations HIE13266 and HIE12106R2) were processed using magnetization. Particle lot HIE13266 was produced using the inventive production method with continuous washing in a microfiltration unit (see Examples 2 and 3). Particle lot HIE12106R2 was produced by repeated sequential washing (see WO 03/058649 A1) based on Bayoxide E 8707. Both supernatants were then subjected to a quantitative RT-PCR intervention:

The so-called quantitative RT (reverse transcription)-PCR intervention was carried out on the MX 4000 from Stratagene. As part of this, 5 μl of the supernatants of both of the particle supernatants, and 5 μl of water as a control, was added to 20 μl of Mastermix. This contains the following components: 400 nM Primer A, 400 nM Primer B, 10 ng MCF-7 RNA (Ambion), Taqman Primer 200 nM, 1× Buffer A, 5 mM $MgCl_2$; 1.2 mM dNTPs, 8 U RNaseInhibitor, 20 U MuLV Reverse Transcriptase, 1.25 U Taq Gold (all from Applied Biosystems). The PCR program was: 30 min at 45° C., 10 min at 95° C., 45 cycles of 15 seconds at 96° C., 60 seconds at 63° C. and 30 sec at 72° C.

The preparations were placed in a 96-well microtiter plate (Stratagene), sealed and placed in the analysis device. On completion of the run and using device software, an individual $C_1$ value (number of cycle at which the selected base value intersects the amplification curve) was assigned to each sample at a selected basic value (fluorescence intensity) in the exponential amplification range of the signal curves.

Figure 2:
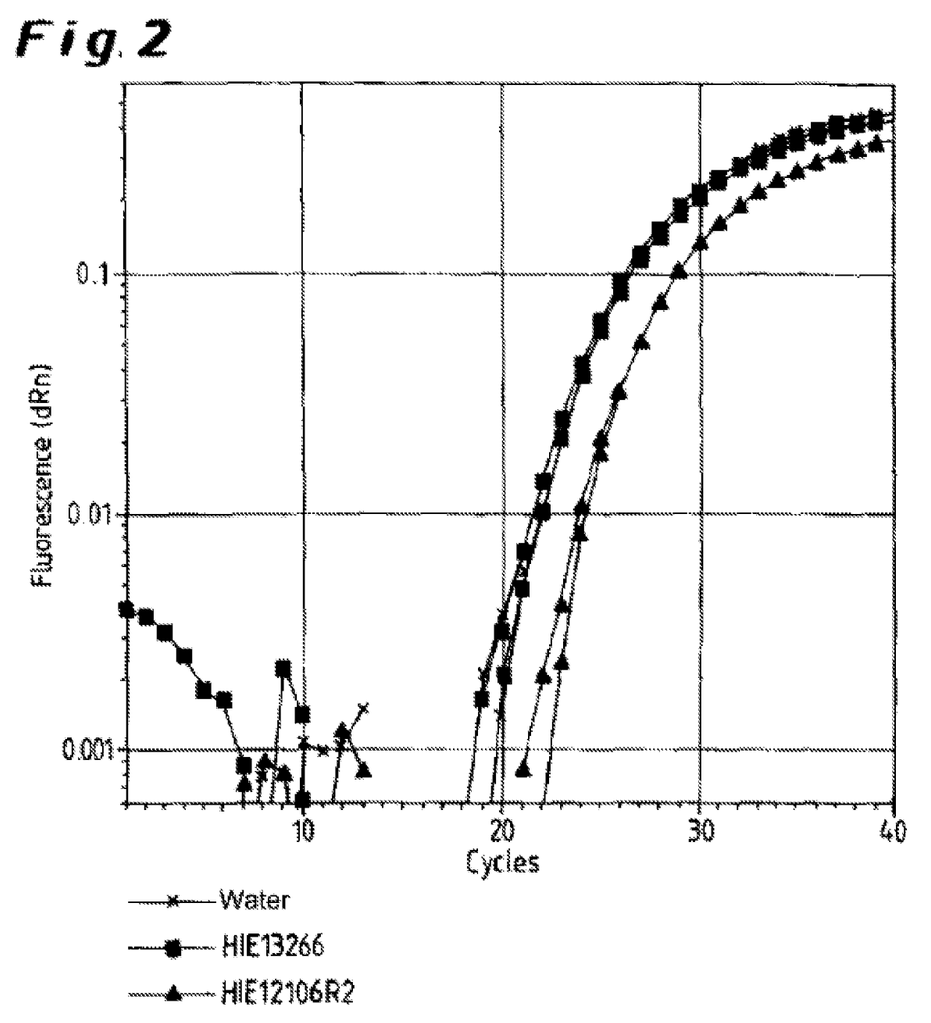
FIG. 2 illustrates amplification curves with supernatants of particles comparable with the amplification curves with water.

As can be seen from FIG. 2, the amplification curves with supernatants of particles HIE13266 are comparable with the amplification curves with water as a sample. On the other hand, a shift of the amplification curves of approximately 3 Ct values with supernatants from HIE12106R2 can be seen on the right-hand side, which indicates interference or negative influence on the efficiency of the RT-PCR.

What is claimed is:

1. A method of purification of nucleic acid from a biological sample, comprising:
dissolving the biological sample containing a nucleic acid of HCV or HIV into a sample solution;
forming silica-coated magnetic particles by depositing initial-silicate layers on magnetic particles and continuously diluting using cross-flow microfiltration to reduce a pH value to a neutral pH value;
adding the silica-coated magnetic particles to the sample solution;
incubating the sample solution at a temperature at which the nucleic acid bonds to the silica-coated magnetic particles;
applying, at a first time, a first magnetic field to the sample solution;
removing constituents not bonded to the silica-coated magnetic particles;
removing unspecifically bonded molecules from the nucleic acid by applying and removing a washing buffer;
separating nucleic acid from the silica-coated magnetic particles by adding an elution buffer; and
applying, at a second time, a second magnetic field and separating eluate with the nucleic acid of HCV or HIV.

2. The method of claim 1, wherein the biological sample is infected with HCV.

3. The method of claim 1, wherein the biological sample is infected with HIV.

4. The method of claim 1, wherein the nucleic acid is RNA of HCV or HIV.

5. The method of claim 1, wherein prior to continuously diluting, carrying out a fractionated centrifugation.

6. A method for purification of nucleic acids from a biological sample in viral diagnostics, comprising:
dissolving the biological sample containing nucleic acid of HCV or HIV into a sample solution;
forming silica-coated magnetic particles by depositing initial-silicate layers on magnetic particles and continuously diluting using cross-flow microfiltration to reduce a pH value to a neutral pH value;
adding the silica-coated magnetic particles to the sample solution;
incubating the sample solution at a temperature at which the nucleic acid bonds to the silica-coated magnetic particles;
applying a magnetic field to the sample solution;
removing constituents not bonded to the silica-coated magnetic particles;
removing unspecifically bonded molecules from the nucleic acid by applying and removing a washing buffer a plurality of times;
separating the nucleic acid from the silica-coated magnetic particles by adding an elution buffer;
applying another magnetic field and separating eluate with the nucleic acid of HCV and HIV; and
analyzing nucleic acid of HCV or HIV obtained from eluate.

7. The method of claim 6, further comprising:
prior to adding the silica-coated magnetic particles to the sample solution, carrying out a fractionated centrifugation on the silica-coated magnetic particles; and
subjecting the nucleic acid obtained from the eluate to an amplification reaction prior to analyzing.

8. The method of claim 7, wherein the amplification reaction is selected from a group consisting of a polymerase chain reaction, a transcription mediated amplification, a ligase chain reaction, and a nucleic acid sequence based amplification.

9. The method of claim 7, wherein the nucleic acid obtained from the amplification reaction includes nucleic acid of HCV.

10. The method of claim 7, wherein the nucleic acid obtained from the amplification reaction includes nucleic acid of HIV.

\* \* \* \* \*